United States Patent
Côté et al.

(10) Patent No.: US 11,919,912 B2
(45) Date of Patent: Mar. 5, 2024

(54) MODULATORS OF METHYL MODIFYING ENZYMES, COMPOSITIONS AND USES THEREOF

(71) Applicant: Constellation Pharmaceuticals, Inc., Boston, MA (US)

(72) Inventors: Alexandre Côté, Cambridge, MA (US); Avinash Khanna, Cambridge, MA (US); Ludivine Moine, Cambridge, MA (US)

(73) Assignee: Constellation Pharmaceuticals, Inc., Boston, MA (US)

( * ) Notice: Subject to any disclaimer, the term of this patent is extended or adjusted under 35 U.S.C. 154(b) by 745 days.

(21) Appl. No.: 17/057,225

(22) PCT Filed: May 17, 2019

(86) PCT No.: PCT/US2019/032926
§ 371 (c)(1),
(2) Date: Nov. 20, 2020

(87) PCT Pub. No.: WO2019/226491
PCT Pub. Date: Nov. 28, 2019

(65) Prior Publication Data
US 2021/0206776 A1    Jul. 8, 2021

Related U.S. Application Data

(60) Provisional application No. 62/674,141, filed on May 21, 2018.

(51) Int. Cl.
*C07D 491/056* (2006.01)
*A61K 31/435* (2006.01)
*A61P 35/00* (2006.01)

(52) U.S. Cl.
CPC .......... *C07D 491/056* (2013.01); *A61P 35/00* (2018.01)

(58) Field of Classification Search
CPC .............................. A61K 31/435; A61P 35/00
USPC ....................................................... 514/291
See application file for complete search history.

(56) References Cited

U.S. PATENT DOCUMENTS

| | | | |
|---|---|---|---|
| 5,221,599 A | 6/1993 | Katoh et al. | |
| 5,296,497 A | 3/1994 | Hartog et al. | |
| 5,385,917 A | 1/1995 | Ueno et al. | |
| 5,514,505 A | 5/1996 | Limburg et al. | |
| 5,626,791 A | 5/1997 | Fenkl et al. | |
| 5,629,200 A | 5/1997 | Furukawa et al. | |
| 6,051,575 A | 4/2000 | Blythin et al. | |
| 10,689,371 B2 | 6/2020 | Cote et al. | |
| 2004/0092740 A1 | 5/2004 | Dumas et al. | |
| 2005/0245529 A1 | 11/2005 | Stenkamp et al. | |
| 2008/0194803 A1 | 8/2008 | Sinclair et al. | |
| 2009/0030197 A1 | 1/2009 | Chew et al. | |
| 2009/0047278 A1 | 2/2009 | Owa et al. | |
| 2009/0143353 A1 | 6/2009 | Kawakami et al. | |
| 2015/0051163 A1 | 2/2015 | Keilhack et al. | |
| 2015/0126522 A1 | 5/2015 | Burgess et al. | |
| 2015/0361067 A1 | 12/2015 | Collins et al. | |
| 2016/0159782 A1 | 6/2016 | Yu et al. | |
| 2016/0222047 A1 | 8/2016 | Zhong et al. | |
| 2017/0073335 A1 | 3/2017 | Kanno et al. | |
| 2017/0334891 A1 | 11/2017 | Knight et al. | |
| 2017/0355708 A1 | 12/2017 | Jefson et al. | |
| 2018/0200238 A1 | 7/2018 | Watanabe et al. | |
| 2019/0343816 A1 | 11/2019 | Yamano et al. | |
| 2020/0317651 A1 | 10/2020 | Cote et al. | |
| 2022/0251073 A1 | 8/2022 | Banda et al. | |
| 2022/0257577 A1 | 8/2022 | Bradley | |

FOREIGN PATENT DOCUMENTS

| | | |
|---|---|---|
| BR | PI0704074 A2 | 1/2010 |
| CA | 2100642 A1 | 1/1994 |
| CN | 101851218 A | 10/2010 |
| CN | 102958937 A | 3/2013 |
| CN | 104168890 A | 11/2014 |
| CN | 104968646 A | 10/2015 |
| CN | 105102446 A | 11/2015 |
| CN | 106132954 A | 11/2016 |
| CN | 106727549 A | 5/2017 |
| CN | 108135908 A | 6/2018 |
| CN | 108136011 A | 6/2018 |
| CN | 108314677 A | 7/2018 |
| CN | 111989325 A | 11/2020 |
| DE | 10148617 A1 | 4/2003 |
| DE | 10219294 A1 | 11/2003 |
| EP | 372657 A1 | 6/1990 |

(Continued)

OTHER PUBLICATIONS

Hatta et al., Development and future prospect EZH1/2 dual inhibitor for malignant lymphoma. Hematology. Jan. 1, 2018;77(4):457-463.
Fujita et al., Dual inhibition of EZH1/2 breaks the quiescence of leukemia stem cells in acute myeloid leukemia. Leukemia. Apr. 2018;32(4):855-864.
Gaikwad et al., The Use of Bioisosterism in Drug Design and Molecular Modification. Am J PharmTech Res. 2012;2(4):1-23.
Kung et al., Design and Synthesis of Pyridone-Containing 3,4-Dihydroisoquinoline-1(2H)-ones as a Novel Class of Enhancer of Zeste Homolog 2 (EZH2) Inhibitors. J Med Chem. Sep. 22, 2016;59(18):8306-25.

(Continued)

*Primary Examiner* — Raymond J Henley, III
(74) *Attorney, Agent, or Firm* — McCarter & English, LLP; Michael J. DeGrazia

(57) ABSTRACT

Provided are novel compounds of Formula (I): Formula (I); and pharmaceutically acceptable salts thereof, which are useful for treating a variety of diseases, disorders or conditions, associated with methyl modifying enzymes. Also provided are pharmaceutical compositions comprising the novel compounds of Formula (I), pharmaceutically acceptable salts thereof, and methods for their use in treating one or more diseases, disorders or conditions, associated with methyl modifying enzymes.

18 Claims, No Drawings

(56) References Cited

FOREIGN PATENT DOCUMENTS

| | | |
|---|---|---|
| EP | 1384713 A1 | 1/2004 |
| EP | 3121175 A1 | 1/2017 |
| EP | 3329917 A1 | 6/2018 |
| EP | 3929199 A1 | 12/2021 |
| JP | S63-017850 A | 1/1988 |
| JP | H02-255673 A | 10/1990 |
| JP | H02-255674 A | 10/1990 |
| JP | H02-269352 A | 11/1990 |
| JP | H02-282354 A | 11/1990 |
| JP | H03-130280 A | 6/1991 |
| JP | H04-046175 A | 2/1992 |
| JP | H10-287654 A | 10/1998 |
| JP | 2006-145294 A | 6/2006 |
| JP | 2010-254629 A | 11/2010 |
| JP | 2019-168611 A | 10/2019 |
| RU | 2509770 C2 | 3/2014 |
| WO | 1997/26884 A1 | 7/1997 |
| WO | 1997/43273 A1 | 11/1997 |
| WO | 1999/21422 A1 | 5/1999 |
| WO | 2000/018761 A1 | 4/2000 |
| WO | 2002/016333 A2 | 2/2002 |
| WO | 2002/016352 A1 | 2/2002 |
| WO | 2002/006229 A3 | 7/2002 |
| WO | 2002/055072 A1 | 7/2002 |
| WO | 2002/074307 A1 | 9/2002 |
| WO | 2002/081443 A1 | 10/2002 |
| WO | 2002/085895 A1 | 10/2002 |
| WO | 2003/029223 A1 | 4/2003 |
| WO | 2003/035635 A1 | 5/2003 |
| WO | 2003/059258 A2 | 7/2003 |
| WO | 2003/062392 A2 | 7/2003 |
| WO | 2003/075858 A2 | 9/2003 |
| WO | 2003/086386 A1 | 10/2003 |
| WO | 2002/016327 | 11/2003 |
| WO | 2003/059898 A3 | 2/2004 |
| WO | 2004/013120 A1 | 2/2004 |
| WO | 2004/022023 A1 | 3/2004 |
| WO | 2004/026274 A1 | 4/2004 |
| WO | 2005/011686 A1 | 2/2005 |
| WO | 2005/030704 A1 | 4/2005 |
| WO | 2005/049008 A1 | 6/2005 |
| WO | 2005/049627 A1 | 6/2005 |
| WO | 2005/100321 A1 | 10/2005 |
| WO | 2005/110410 A2 | 11/2005 |
| WO | 2005/112932 A2 | 12/2005 |
| WO | 2006/003068 A2 | 1/2006 |
| WO | 2006/014136 A1 | 2/2006 |
| WO | 2006/040318 A2 | 4/2006 |
| WO | 2006/046914 A1 | 5/2006 |
| WO | 2006/058648 A2 | 6/2006 |
| WO | 2006/090930 A1 | 8/2006 |
| WO | 2006/096807 A1 | 9/2006 |
| WO | 2006/103449 A2 | 10/2006 |
| WO | 2006/110447 A2 | 10/2006 |
| WO | 2006/125119 A1 | 11/2006 |
| WO | 2006/127205 A2 | 11/2006 |
| WO | 2006/129609 A1 | 12/2006 |
| WO | 2006/130403 A1 | 12/2006 |
| WO | 2007/011820 A2 | 1/2007 |
| WO | 2007/014154 A2 | 2/2007 |
| WO | 2007/019083 A1 | 2/2007 |
| WO | 2007/081630 A2 | 7/2007 |
| WO | 2007/085136 A1 | 8/2007 |
| WO | 2007/107758 A1 | 9/2007 |
| WO | 2007/138037 A1 | 12/2007 |
| WO | 2008/027648 A2 | 3/2008 |
| WO | 2008/029168 A2 | 3/2008 |
| WO | 2008/052256 A1 | 5/2008 |
| WO | 2008/054252 A1 | 5/2008 |
| WO | 2008/141081 A1 | 11/2008 |
| WO | 2009/054914 A1 | 4/2009 |
| WO | 2009/136995 A2 | 11/2009 |
| WO | 2010/008761 A1 | 1/2010 |
| WO | 2010/019772 A2 | 2/2010 |
| WO | 2010/137738 A1 | 12/2010 |
| WO | 2011/004018 A1 | 1/2011 |
| WO | 2011/006653 A1 | 1/2011 |
| WO | 2011/084657 A1 | 7/2011 |
| WO | 2011/091757 A1 | 8/2011 |
| WO | 2011/156775 A2 | 12/2011 |
| WO | 2011/159297 A1 | 12/2011 |
| WO | 2012/013725 A1 | 2/2012 |
| WO | 2012/016879 A1 | 2/2012 |
| WO | 2012/036278 A1 | 3/2012 |
| WO | 2012/045196 A1 | 4/2012 |
| WO | 2012/126922 A1 | 9/2012 |
| WO | 2013/025484 A1 | 2/2013 |
| WO | 2013/025584 A1 | 2/2013 |
| WO | 2013/065835 A1 | 5/2013 |
| WO | 2013/142712 A1 | 9/2013 |
| WO | 2014/034898 A1 | 3/2014 |
| WO | 2014/066435 A1 | 5/2014 |
| WO | 2014/124418 A1 | 8/2014 |
| WO | 2014/160401 A1 | 10/2014 |
| WO | 2014/177464 A2 | 11/2014 |
| WO | 2015/034271 A1 | 3/2015 |
| WO | 2015/069110 A1 | 5/2015 |
| WO | 2015/141616 A1 | 9/2015 |
| WO | 2016/038540 A1 | 3/2016 |
| WO | 2016/130396 A1 | 8/2016 |
| WO | 2017/018499 A1 | 2/2017 |
| WO | 2017/040190 A1 | 3/2017 |
| WO | 2017/121648 A1 | 7/2017 |
| WO | 2017/139414 A1 | 8/2017 |
| WO | 2018/013789 A1 | 1/2018 |
| WO | 2018/135556 A1 | 7/2018 |
| WO | 2018/170513 A1 | 9/2018 |
| WO | 2018/218070 A2 | 11/2018 |
| WO | 2019/084271 A1 | 5/2019 |
| WO | 2019/086890 A1 | 5/2019 |
| WO | 2019/124537 A1 | 6/2019 |
| WO | 2019/140322 A1 | 7/2019 |
| WO | 2019/191558 A1 | 10/2019 |
| WO | 2019/204490 A1 | 10/2019 |

OTHER PUBLICATIONS

Venkatesan et al., Bioisoterism Review—an Biological Modification. World Journal of Pharmacy and Pharmaceutical Sciences. 2017;6(9):1918-49.
U.S. Appl. No. 16/387,851, filed Apr. 18, 2019, U.S. Pat. No. 10,689,371, Issued.
U.S. Appl. No. 16/856,454, filed Apr. 23, 2020, U.S. Pat. No. 11,274,095, Issued.
U.S. Appl. No. 17/591,149, filed Feb. 2, 2022, Abandoned.
U.S. Appl. No. 17/941,276, filed Sep. 9, 2022, Abandoned.
U.S. Appl. No. 18/140,730, filed Apr. 28, 2023, Pending.
U.S. Appl. No. 17/628,947, filed Jan. 21, 2022, 2022/0251073, Published.
U.S. Appl. No. 17/628,948, filed Jan. 21, 2022, 2022/0257577, Published.

MODULATORS OF METHYL MODIFYING ENZYMES, COMPOSITIONS AND USES THEREOF

RELATED APPLICATIONS

This application is a 35 U.S.C. § 371 national stage filing of International Application No. PCT/US2019/032926, filed May 17, 2019, which claims the benefit of priority to U.S. Provisional Application No. 62/674,141, filed May 21, 2018. The entire contents of each of the aforementioned applications are incorporated herein by reference.

BACKGROUND

Eukaryotic chromatin is composed of macromolecular complexes called nucleosomes. A nucleosome has 147 base pairs of DNA wrapped around a protein octamer having two subunits of each of histone protein H2A, H2B, H3, and H4. Histone proteins are subject to post-translational modifications which in turn affect chromatin structure and gene expression. One type of post-translational modification found on histones is methylation of lysine and arginine residues. Histone methylation plays a critical role in the regulation of gene expression in eukaryotes. Methylation affects chromatin structure and has been linked to both activation and repression of transcription (Zhang and Reinberg, Genes Dev. 15:2343-2360, 2001). Enzymes that catalyze attachment and removal of methyl groups from histones are implicated in gene silencing, embryonic development, cell proliferation, and other processes.

One class of histone methylases is characterized by the presence of a SET domain, comprising about 130 amino acids. EZH2 is an example of a human SET-domain containing methylase. EZH2 associates with EED (Embryonic Ectoderm Development) and SUZ12 (suppressor of zeste 12 homolog) to form a complex known as PRC2 (Polycomb Group Repressive Complex 2) having the ability to tri-methylate histone H3 at lysine 27 (Cao and Zhang, Mol. Cell 15:57-67, 2004). PRC2 complexes can also include RBAP46 and RBAP48 subunits. Another example is the related methylase EZH1.

The oncogenic activities of EZH2 have been shown by a number of studies in various different cancer types. ~15-20% GCB-DLBCLs harbor a gain-of-function mutation in EZH2 (Y641 residue) and these cells are hypersensitive to EZH2 inhibition both in vitro and in vivo (McCabe et al, 2012; Bradley et al, 2014). In cell line experiments, overexpression of EZH2 induces cell invasion, growth in soft agar, and motility, while knockdown of EZH2 inhibits cell proliferation and cell invasion (Kleer et al., 2003, Proc. Nat. Acad. Sci. USA 100:11606-11611; Varambally et al., (2002), "The polycomb group protein EZH2 is involved in progression of prostate cancer," Nature 419, 624-629). It has been shown that EZH2 represses the expression of several tumor suppressors, including E-cadherin, DAB2IP and RUNX3 among others. In xenograft models, EZH2 knockdown inhibits tumor growth and metastasis. It has been shown that down modulation of EZH2 in murine models blocks prostate cancer metastasis (Min et al., "An oncogene-tumor suppressor cascade drives metastatic prostate cancer by coordinately activating Ras and nuclear factor-kappaB," Nat Med. 2010 March; 16(3):286-94). Recently, it was demonstrated that EZH2 is over-expressed in neuroendocrine tumors and inhibition of EZH2 in mouse tumors restore androgen dependence (Ku et al, Science, 355, 2017). EZH2 overexpression is associated with aggressiveness of certain cancers such as breast cancer (Kleer et al., Proc. Nat. Acad. Sci. USA 100:11606-11611, 2003). Recent studies also suggest that prostate cancer specific oncogenic fusion gene TMPRSS2-ERG induces repressive epigenetic programs via direct activation of EZH2 (Yu et al., "An Integrated Network of Androgen Receptor, Polycomb, and TMPRSS2-ERG Gene Fusions in Prostate Cancer Progression," Cancer Cell. 2010 May 18;17(5):443-454).

Given their role in the regulation of diverse biological processes, methyl modifying enzymes, in particular EZH2 and mutant forms thereof, are attractive targets for modulation.

SUMMARY

It has now been found that compounds described herein, and pharmaceutically acceptable compositions thereof, modulate the activity of EZH2 (See e.g., Table 1). Such compounds include those of structural Formula I:

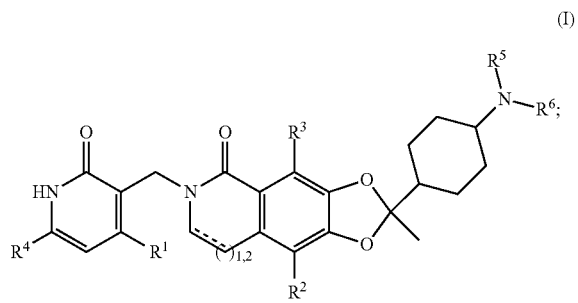

or a pharmaceutically acceptable salt thereof, wherein each of $R^1$, $R^2$, $R^3$, $R^4$, $R^5$, and $R^6$ are defined herein.

The disclosed compounds, pharmaceutically acceptable salts, and pharmaceutically acceptable compositions, are useful for treating a variety of conditions associated with methyl modifying enzymes. These conditions include e.g., one or more cancers.

DETAILED DESCRIPTION

1. General Description of Compounds

Provided are compounds of Formula I:

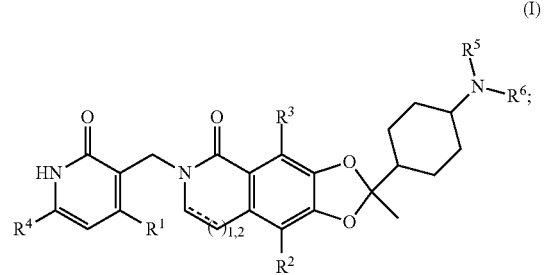

or a pharmaceutically acceptable salt thereof, wherein:
$R^1$ is halo, $(C_1-C_4)$alkyl, halo$(C_1-C_4)$alkyl, $(C_1-C_4)$alkoxy, or halo$(C_1-C_4)$alkoxy, —S$(C_1-C_4)$alkyl, or —S[halo$(C_1-C_4)$alkYl];
$R^2$ is hydrogen, halo, or $(C_1-C_4)$alkyl;
$R^3$ is $(C_1-C_4)$alkyl or halo$(C_1-C_4)$alkyl;
$R^4$ is halo, $(C_1-C_4)$alkyl, or halo$(C_1-C_4)$alkyl;

$R^5$ is hydrogen, $(C_1-C_4)$alkyl, or halo$(C_1-C_4)$alkyl;

$R^6$ is halo, $(C_1-C_4)$alkyl, or halo$(C_1-C_4)$alkyl; or $R^5$ and $R^6$ together with the nitrogen atom to which they are attached form a 4- to 7-membered heterocyclyl optionally substituted with 1 to 3 groups selected from halo, $(C_1-C_4)$alkyl, halo$(C_1-C_4)$alkyl, and —OW;

$R^7$ is $(C_1-C_4)$alkyl, halo$(C_1-C_4)$alkyl, or $(C_3-C_7)$cycloalkyl; and the dashed line represents a single or double bond.

2. Definitions

When used in connection to describe a chemical group that may have multiple points of attachment, a hyphen (-) designates the point of attachment of that group to the variable to which it is defined. For example, —S[halo$(C_1-C_4)$alkyl] means that the point of attachment for this group occurs on the sulfur atom.

The terms "halo" and "halogen" as used herein refer to an atom selected from fluorine (fluoro, —F), chlorine (chloro, —Cl), bromine (bromo, —Br), and iodine (iodo, -I).

The term "alkyl," as used herein, refers to a monovalent saturated, straight- or branched-chain hydrocarbon radical, having unless otherwise specified, 1-4 carbon atoms. Examples of alkyl radicals include, but are not limited to, methyl, ethyl, n-propyl, isopropyl, n-butyl, iso-butyl, and sec-butyl.

The term "haloalkyl" includes mono, poly, and perhaloalkyl groups where the halogens are independently selected from fluorine, chlorine, bromine, and iodine.

"Alkoxy" is an alkyl group which is attached to another moiety via an oxygen linker (—O(alkyl)). Non-limiting examples include methoxy, ethoxy, propoxy, and butoxy.

"Haloalkoxy" is a haloalkyl group which is attached to another moiety via an oxygen atom such as, e.g., but are not limited to —OCHCF$_2$ or —OCF$_3$.

The term "4- to 7-membered heterocyclyl" means a 4-7 membered (e.g., a 4-, 5-, 6- and 7-membered) saturated or partially unsaturated monocyclic heterocyclic ring containing 1 to 4 heteroatoms independently selected from N, O, and S. The terms "heterocycle", "heterocyclyl", "heterocyclyl ring", "heterocyclic group", "heterocyclic moiety", and "heterocyclic radical", are used interchangeably herein. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. Where specified as being optionally substituted or substituted, substituents on a heterocyclyl (e.g., in the case of an optionally substituted heterocyclyl) may be present on any substitutable position and, include, e.g., the position at which the heterocyclyl group is attached.

As used herein, "geometric isomer" refers to isomers that differ in the orientation of substituent atoms in relationship to a cycloalkyl ring, i.e., cis or trans isomers. When a disclosed compound is named or depicted by structure without indicating a particular cis or trans geometric isomer form, it is to be understood that the name or structure encompasses one geometric isomer free of other geometric isomers, mixtures of geometric isomers, or mixtures enriched in one geometric isomer relative to its corresponding geometric isomer. When a particular geometric isomer is depicted, i.e., cis or trans, the depicted isomer is at least 60%, 70%, 80%, 90%, 99% or 99.9% by weight pure relative to the other geometric isomer.

Unless otherwise specified, when the stereochemistry of a disclosed compound is named or depicted by structure, the named or depicted stereoisomer is at least 60%, 70%, 80%, 90%, 99% or 99.9% by weight pure relative to all of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer. Enantiomers may be resolved by methods known to those skilled in the art, for example by formation of diastereoisomeric salts which may be separated, for example, by crystallization; formation of diastereoisomeric derivatives or complexes which may be separated, for example, by crystallization, supercritical fluid or liquid chromatography; selective reaction of one enantiomer with an enantiomer-specific reagent, for example enzymatic esterification; or supercritical fluid or liquid chromatography in a chiral environment, for example on a chiral support for example silica with a bound chiral ligand or in the presence of a chiral solvent. Specific enantiomers may also be synthesized by asymmetric synthesis using optically active reagents, substrates, catalysts or solvents, or by converting one enantiomer into the other by asymmetric transformation.

Unless otherwise specified, when a disclosed compound is named or depicted by structure without indicating the stereochemistry, and the name or structure encompasses more than one enantiomer and/or more than one geometric isomer, the name or structure encompasses one enantiomer and/or geometric isomer of the compound free from the corresponding optical isomer or geometric isomer, a racemic mixture of the compound and mixtures enriched in one enantiomer or geometric isomer relative to its corresponding optical isomer or geometric isomer.

The term "patient," as used herein, means an animal, such as a mammal, and such as a human. The terms "subject" and "patient" may be used interchangeably.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "treatment," "treat," and "treating" refer to reversing, alleviating, or inhibiting the progress of a disease or disorder, or one or more symptoms thereof, as described herein. Treatment may also be continued after symptoms have resolved, for example to delay recurrence.

Disease, disorder, and condition are used interchangeably herein.

The term "effective amount" or "therapeutically effective amount" refers to an amount of a compound described herein that will elicit a biological or medical response of a subject e.g., a dosage of between 0.01-100 mg/kg body weight/day. The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

The compounds described herein may be present in the form of pharmaceutically acceptable salts. For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids).

3. Description of Exemplary Compounds

In a first embodiment, the present disclosure provides a compound of Formula I:

(I)

or a pharmaceutically acceptable salt thereof, wherein the variables are as above for Formula I.

In a second embodiment, the compound of Formula I is of Formula II:

(II)

or a pharmaceutically acceptable salt thereof, wherein the variables are as described above for Formula I.

In a third embodiment, the compound of Formula I or II is of the Formula III:

(III)

or a pharmaceutically acceptable salt thereof, wherein the variables are as described above for Formula I.

In a fourth embodiment, the compound of Formula I, II, or III is of the Formula IV:

(IV)

or a pharmaceutically acceptable salt thereof, wherein the variables are as described above for Formula I.

In a fifth embodiment, $R^1$ in the compound of Formula I, II, III, or IV is halo or —S($C_1$-$C_4$)alkyl, wherein the remaining variables are as described above for Formula I.

In a sixth embodiment, $R^4$ in the compound of Formula I, II, III, or IV is halo or ($C_1$-$C_4$)alkyl, wherein the remaining variables are as described above for Formula I or the fifth embodiment.

In a seventh embodiment, $R^5$ in the compound of Formula I, II, III, or IV is ($C_1$-$C_4$)alkyl, wherein the remaining variables are as described above for Formula I or the fifth or sixth embodiment.

In an eighth embodiment, $R^6$ in the compound of Formula I, II, III, or IV is ($C_1$-$C_4$)alkyl, wherein the remaining variables are as described above for Formula I or the fifth or sixth embodiment.

In a ninth embodiment, $R^5$ and $R^6$ in the compound of Formula I, II, III, or IV are each methyl, wherein the remaining variables are as described above for Formula I or the fifth or sixth embodiment.

In a tenth embodiment, the group and NR⁵R⁶ in the compound of Formula I, II, III, or IV are oriented trans about the cyclohexyl, wherein the variables are as described above for Formula I or the fifth, sixth, seventh, eighth, or ninth embodiment.

In an eleventh embodiment, the group

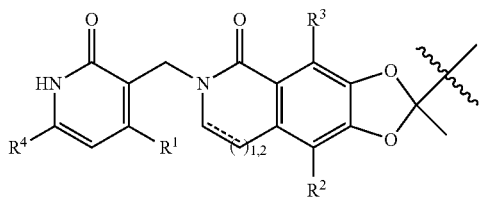

and NR⁵R⁶ in the compound of Formula I, II, III, or IV are oriented cis about the cyclohexyl, wherein the variables are as described above for Formula I or the fifth, sixth, seventh, eighth, or ninth embodiment.

In a twelfth embodiment, the stereochemical configuration of the chiral center of the 1,3-dioxolanyl in the compound of Formula I, II, III, or IV is R, wherein the variables and remaining features are as described above for Formula I or the fifth, sixth, seventh, eighth, ninth, tenth, or eleventh embodiment.

In a thirteenth embodiment, the stereochemical configuration of the chiral center of the 1,3-dioxolanyl in the compound of Formula I, II, III, or IV is S, wherein the variables and remaining features are as described above for Formula I or the fifth, sixth, seventh, eighth, ninth, tenth, or eleventh embodiment.

Specific examples of compounds are provided in the EXEMPLIFICATION section and are included as part of a fourteenth embodiment herein. Pharmaceutically acceptable salts as well as the neutral forms of these compounds are also included. In one aspect, the present disclosure includes racemic forms of any compound described herein.

4. Uses, Formulation and Administration

In some embodiments, the present disclosure provides a composition comprising a compound described herein or a pharmaceutically acceptable derivative thereof and a pharmaceutically acceptable carrier. The amount of compound in a provided composition is such that is effective to measurably modulate a histone methyl modifying enzyme, or a mutant thereof, in a biological sample or in a patient.

In certain embodiments, a composition described herein is formulated for administration to a patient in need of such composition. Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions described herein may be aqueous or oleaginous suspension. These suspensions may be formulated according to techniques known in the art using suitable dispersing or wetting agents and suspending agents.

In some embodiments, the compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

Compounds and compositions described herein are generally useful for the modulating of activity of one or more enzymes involved in epigenetic regulation and in particular EZH1 and EZH2 and, even more specifically EZH2 and mutant forms thereof. In some embodiments, compounds described herein down-regulate or suppress the activity of EZH2. In some embodiments, compounds described herein are antagonists of EZH2 activity. In some embodiments, compounds described herein down-regulate or suppress the activity of EZH1. In some embodiments, compounds described herein are antagonists of EZH1 activity.

In some embodiments, compounds and compositions described herein are useful in treating diseases and/or disorders associated with overexpression of EZH1 or EZH2 and/or expression of a mutant form of EZH2, such as those mutant forms that alter EZH2 substrate activity. The study of EZH2 deletions, missense and frameshift mutations suggest that EZH2 functions as a tumor suppressor in blood disorders such as myelodysplastic syndromes (MDS) and myeloid malignancies (Ernst et al., Nat Genet. 2010 August; 42(8):722-6; Nikoloski et al., Nat Genet. 2010 August; 42(8):665-7). In some embodiments, compounds and compositions described herein are useful in treating diseases and/or disorders associated with the presence of EZH2 having a Y641N, Y641C, Y641F, Y641H, Y641S, A677G, or A687 mutation. In a particular aspect of this embodiment, the EZH2 has a Y641N mutation.

In some embodiments, the present disclosure provides a method of treating a subject suffering from a disease and/or disorder associated with overexpression of EZH1 or EZH2 and/or expression of a mutant form of EZH2 comprising the step of administering a compound described herein, or a pharmaceutically acceptable salt or composition thereof. In some embodiments, the above method additionally comprises the preliminary step of determining if the subject is overexpressing EZH2 or expressing a mutant form of EZH2.

In some embodiments, the disease or disorder associated with the presence of a mutant form of EZH2 is a human B cell lymphoma. In some embodiments, the disease and/or disorder associated with the presence of Y641N EZH2 is follicular lymphoma or diffuse large-B-cell lymphoma. In some embodiments, compounds or compositions described herein are useful in treating blood disorders, such as myelodysplastic syndromes, leukemia, anemia and cytopenia. Sneeringer et al., "Coordinated activities of wild-type plus mutant EZH2 drive tumor-associated hypertrimethylation of lysine 27 on histone H3 (H3K27) in human B-cell lymphomas," Sneeringer et al., Proc. Natl Acad. Sci. 2010 December; 109(48):20980-20985.

In some embodiments, compounds and compositions described herein are useful in treating diseases and/or disorders associated with cellular proliferation. In some embodiments, compounds and compositions described herein are useful in treating diseases and/or disorders associated with misregulation of cell cycle or DNA repair. In some embodiments, compounds and compositions described herein are useful in treating cancer.

In one aspect, cancers that may be treated by the compounds, compositions and methods described herein include, but are not limited to Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, clear cell carcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

In one aspect, the cancer treated by the compounds, compositions, and methods described herein is selected from adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NKcell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angio sarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor Tlymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor.

In one aspect, the cancer treated by the compounds, compositions, and methods described herein is selected from adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, acute myeloid leukemia (AML), diffuse large B-cell lymphoma (DLBCL), ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, and Wilms' tumor.

In one aspect, the cancer treated by the compounds, compositions, and methods described herein are selected from breast cancer, prostate cancer, colon cancer, renal cell carcinoma, glioblastoma multiforme cancer, bladder cancer, melanoma, bronchial cancer, lymphoma and liver cancer.

Also provided is the use of a compound described herein, or a pharmaceutically acceptable salt thereof, or a composition comprising a disclosed compound or pharmaceutically acceptable salt thereof, for the manufacture of a medicament for treating a condition described herein. Also provided is a compound described herein, or a pharmaceutically acceptable salt thereof, or a composition comprising a disclosed compound or pharmaceutically acceptable salt thereof, for use in treating a condition described herein.

Exemplification

The representative examples that follow are intended to help illustrate the invention, and are not intended to, nor should they be construed to, limit the scope of the invention.

Preparation of Intermediates

Intermediate 1: 3-(aminomethyl)-6-methyl-4-(methylthio)pyridin-2(1H)-one(hydrochloride salt)

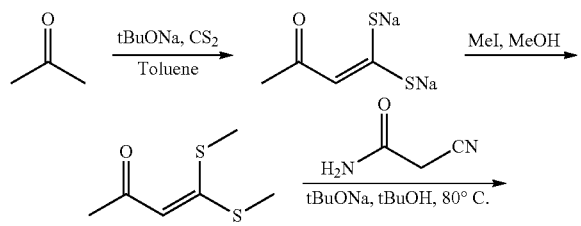

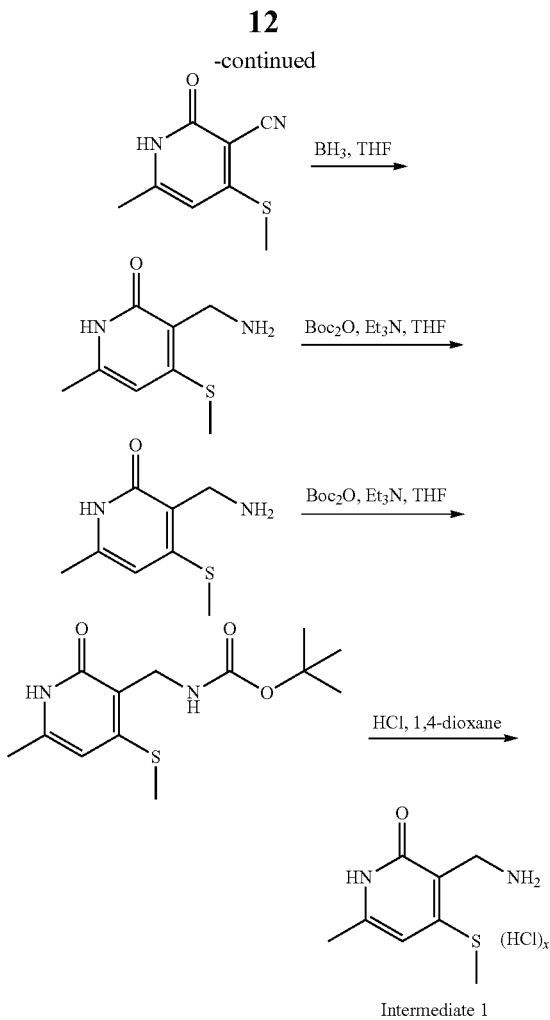

Intermediate 1

Step 1: Synthesis of Sodium 3-Oxobut-1-Ene-1,1-Bis(Thiolate)

A mixture of sodium tert-butoxide (16.6 g, 172 mmol) in toluene (30 mL) was degassed under vacuum and purged with nitrogen (3 cycles). Acetone (5.0 g, 6.4 mL, 86 mmol) was then added at 0° C. followed by the slow addition of carbon disulfide (6.6 g, 5.24 mL, 86 mmol). The resulting mixture was stirred at 0° C. for 4 h, then filtered. The filter cake was dried under vacuum to give the title compound (15.4 g, crude) as a yellow solid, which was used in the next step without further purification.

Step 2: Synthesis of 4,4-Bis(Methylthio)but-3-En-2-One

To a solution of sodium 3-oxobut-1-ene-1,1-bis(thiolate) (15.4 g, 86.4 mmol) in methanol (90 mL) was slowly added iodomethane (24.5 g, 10.7 mL, 173 mmol). The mixture was stirred at 70° C. for 1 h then concentrated to dryness. Water (30 mL) was added and the desired product was extracted with ethyl acetate (60 mL×3). The combined organic layers were dried over sodium sulfate and concentrated under reduced pressure to give the title compound (6.8 g, 42% yield) as a brown oil, which was used in the next step without further purification. LCMS [M+H]$^+$ m/z: calc'd 163.0; found 163.0. $^1$H NMR (400 MHz, chloroform-d) δ 6.02 (s, 1H), 2.45 (s, 3H), 2.43 (s, 3H), 2.15 (s, 3H).

Step 3: Synthesis of 6-Methyl-4-(Methylthio)-2-Oxo-1,2-Dihydropyridine-3-Carbonitrile To a solution of 4,4-bis(methylthio)but-3-en-2-one (2.9 g, 18 mmol) and 2-cyanoacetamide (1.5 g, 18 mmol) in tertbutanol (50 mL) was added sodium tert-butoxide (1.9 g, 20 mmol). The mixture was stirred at 80° C. for 12 h (two batches of the reaction were performed and combined at this stage). Water (20 mL) was added and the pH adjusted to 5-6 with 10% hydrochloric acid. The resulting mixture was filtered, and the filter cake was washed with petroleum ether (20 mL×2) then the cake was dried under vacuum to give the title compound (4.8 g, 74% yield) as an off-white solid, which was used in the next step without further purification. LCMS [M+H]$^+$ m/z: calc'd 181.0; found 181.0. $^1$H NMR (400 MHz, dimethylsulfoxide-d 6) δ 6.27 (s, 1H), 2.56 (s, 3H), 2.25 (s, 3H).

Step 4: Synthesis of 3-(Aminomethyl)-6-Methyl-4-(Methylthio)Pyridin-2(1H)-One

A mixture of 6-methyl-4-(methylthio)-2-oxo-1,2-dihydropyridine-3-carbonitrile (3.6 g, 20 mmol) in tetrahydrofuran (50 mL) was degassed under vacuum and purged with nitrogen (3 cycles). Borane dimethylsulfide complex (10 M, 8.0 mL, 80 mmol) was then slowly added at 0° C. before the reaction mixture was warmed to 70° C. and stirred for 2 h. Methanol (15 mL) was slowly added at 0° C. to quench the reaction before the mixture was concentrated under reduced pressure to give the title compound (3.8 g, crude), as a light yellow solid, which was used in the next step without further purification. LCMS [M+H]$^+$ m/z: calc'd 185.1; found 185.0.

Step 5: Synthesis of Tert-Butyl ((6-Methyl-4-(Methylthio)-2-Oxo-1,2-Dihydropyridin-3-Yl)Methyl)Carbamate To a solution of 3-(aminomethyl)-6-methyl-4-(methylthio)pyridin-2(1H)-one (3.6 g, 20 mmol) in tetrahydrofuran (80 mL) was added triethylamine (5.9 g, 8.1 mL, 59 mmol). The mixture was stirred for 30 min before di-tert-butyl dicarbonate (6.4 g, 29 mmol) was added and the reaction stirred at 25° C. for 12 h. The reaction mixture was then concentrated to dryness under reduced pressure, before water (35 mL) was added and the desired product extracted with a 5:1 mixture of petroleum ether/ethyl acetate (30 mL×3). The combined organic layers were dried over sodium sulfate and concentrated to give the title compound (5.8 g, crude) as a white solid, which was used in the next step without further purification. LCMS [M+H]$^+$ m/z: calc'd 285.12; found 284.9. $^1$H NMR (400 MHz, dimethylsulfoxide-d 6) δ 6.05 (s, 1H), 4.03-4.00 (m, 2H), 2.42 (s, 3H), 2.15 (s, 3H), 1.39 (s, 9H).

Step 6: Synthesis of 3-(Aminomethyl)-6-Methyl-4-(Methylthio)Pyridin-2(1H)-One (Hydrochloride Salt)

To a solution of hydrogen chloride in 1,4-dioxane (4 M, 100 mL, 400 mmol) at 25° C. was added tert-butyl ((6-methyl-4-(methylthio)-2-oxo-1,2-dihydropyridin-3-yl)methyl)carbamate (5.0 g, 17.6 mmol). The reaction mixture was stirred at 25° C. for 2 h then concentrated to dryness under reduced pressure. The residue was washed with dichloromethane (30 mL×2) and ethyl acetate (30 mL) to give the title compound (4.5 g, crude, HCl salt) as a yellow solid, which was used in the next step without further purification. LCMS [M+H]$^+$ m/z: calc'd 185.1; found 185.0. $^1$H NMR (400 MHz, D$_2$O) δ 6.31 (s, 1H), 4.03 (s, 2H), 2.41 (s, 3H), 2.18 (s, 3H).

Example 1: 9-Chloro-2-(Trans-4-(Dimethylamino)Cyclohexyl)-2,4-Dimethyl-6-((6-Methyl-4-(Methylthio)-2-Oxo-1,2-Dihydropyridin-3-Yl)Methyl)-7,8-Dihydro-[1,3]Dioxolo[4,5-g]Isoquinolin-5(6H)-One

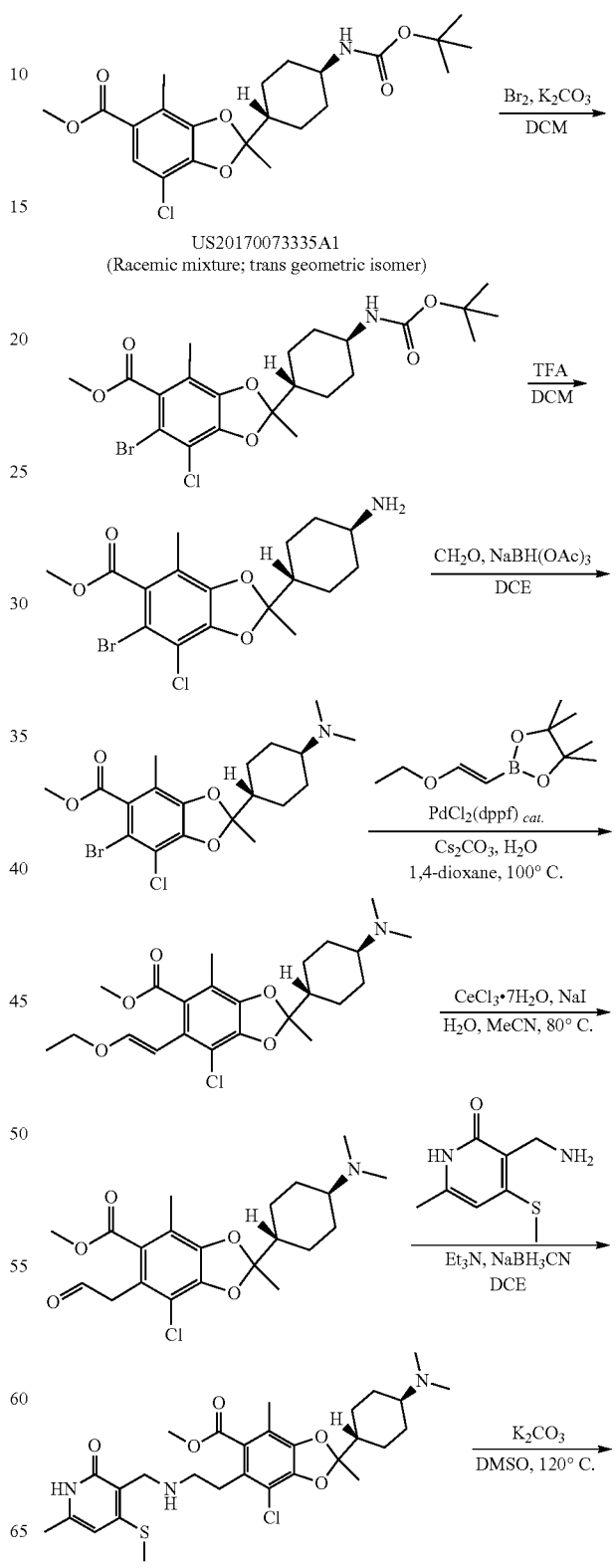

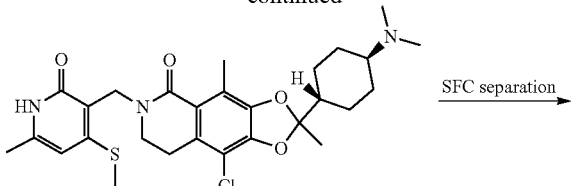

Example 1
(Racemic mixture; trans geometric isomer)

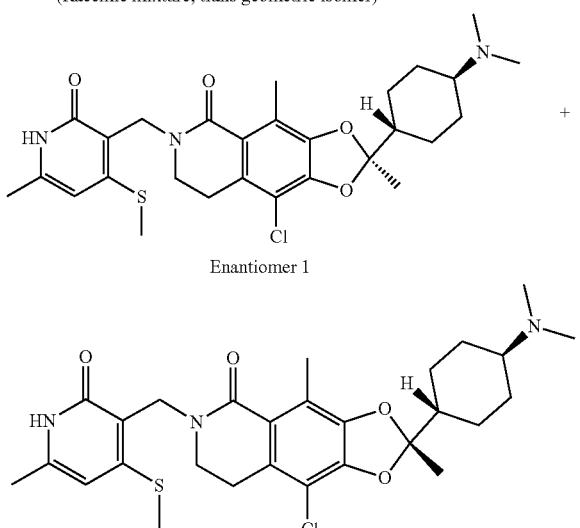

Enantiomer 1

Enantiomer 2
Example 1
(Single enantiomer; trans geometric isomer)

Step 1: Synthesis of Methyl 6-Bromo-7-Chloro-2-(Trans-4-(Dimethylamino)Cyclohexyl)-2,4-Dimethylbenzo[d][1,3] Dioxole-5-Carboxylate To a solution of methyl 2-(trans-4-((tert-butoxycarbonyl)amino)cyclohexyl)-7-chloro-2,4-dimethylbenzo[d][1,3]dioxole-5-carboxylate (7 g, 15.9 mmol) (prepared according to the procedure described in the patent application US2017/0073335 A1) in dichloromethane (80 mL) was added potassium carbonate (2.22 g, 15.9 mmol) followed by dropwise addition of bromine (3.25 mL, 63.6 mmol) at room temperature. The mixture was stirred at room temperature for 30 min (or until complete consumption of the starting material), then quenched with a saturated solution of sodium thiosulfate. The organic layer was separated, and the aqueous layer was extracted three times with dichloromethane. The combined organic layers were washed with brine, dried over sodium sulfate, filtered and concentrated under reduced pressure to give the title compound (theoretical yield 8 g) as a solid which was used in the next step without further purification. LCMS [M+Na]$^+$ m/z: calc'd 540.1; found 540.2.

Step 2: Synthesis of Methyl 2-(Trans-4-Aminocyclohexyl)-6-Bromo-7-Chloro-2,4-Dimethylbenzo[d][1,3]Dioxole-5-Carboxylate Trifluoroacetic Acid Salt To a solution of methyl 6-bromo-7-chloro-2-(trans-4-(dimethylamino)cyclohexyl)-2,4-dimethylbenzo[d][1,3]dioxole-5-carboxylate (8 g, 15.4 mmol) in dichloromethane (31 mL) was added trifluoroacetic acid (7.70 mL) at room temperature. This mixture was stirred at room temperature for 15 min, then concentrated to dryness under reduced pressure to give the title compound (theoretical yield 8.20 g) as a solid which was used in the next step without further purification. LCMS [M+H]$^+$ m/z: calc'd 418.0; found 418.1.

Step 3: Synthesis of Methyl 6-Bromo-7-Chloro-2-(Trans-4-(Dimethylamino)Cyclohexyl)-2,4-Dimethylbenzo[d][1,3] Dioxole-5-Carboxylate To a solution of methyl 2-(trans-4-aminocyclohexyl)-6-bromo-7-chloro-2,4-dimethylbenzo[d][1,3]dioxole-5-carboxylate trifluoroacetic acid salt (8.20 g, 15.4 mmol) in dichloroethane (77 mL) was added formaldehyde (37 wt % in water) (12.3 mL, 154 mmol) at room temperature, followed by the addition of sodium triacetoxyborohydride (16.3 g, 77.0 mmol). The reaction was stirred at room temperature for 15 min then quenched with a saturated solution of sodium bicarbonate. The organic layer was separated, and the aqueous layer was extracted three times with dichloromethane. The combined organic layers were washed with brine, dried over sodium sulfate, filtered and concentrated to dryness under reduced pressure. The residue was purified by flash chromatography (normal phase KP-NH column, gradient 0 to 100% ethyl acetate in heptane) to give the title compound (5.8 g, 78% yield over three steps) as a light-yellow oil. LCMS [M+H]$^+$ m/z: calc'd 446.1; found 446.3.

Step 4: Synthesis of Methyl 7-Chloro-2-(Trans-4-(Dimethylamino)Cyclohexyl)-6-(2-Ethoxyvinyl)-2,4-Dimethylbenzo[d][1,3]Dioxole-5-Carboxylate A mixture of methyl 6-bromo-7-chloro-2-(trans-4-(dimethylamino)cyclohexyl)-2,4-dimethylbenzo[d][1,3]dioxole-5-carboxylate (4.27 g, 9.55 mmol), [1,1'-bis(diphenylphosphino)ferrocene]dichloro palladium(II) complex with dichloromethane (1.55 g, 1.91 mmol), cesium carbonate (9.31 g, 28.6 mmol), 1,4-dioxane (35 mL) and water (5 mL) was degassed (four vacuum/nitrogen refill cycles) prior to adding a solution of 2-[(E)-2-ethoxyethenyl]-4,4,5,5-tetramethyl-1,3,2-dioxaborolane (3.78 g, 19.1 mmol) in 1,4-dioxane (15 mL). The resulting black reaction mixture was heated at 100° C. for 24 h then cooled to room temperature, diluted with ethyl acetate and filtered. The filtrate was washed with water and the aqueous layer was extracted with ethyl acetate three times. The combined organic layers were washed with brine, dried over sodium sulfate, filtered and concentrated under reduced pressure. The residue was purified by flash chromatography (normal phase KP-NH column, gradient 0 to 40% ethyl acetate in heptane) to give the title compound (3.5 g, 84% yield) as a thick yellowish oil. LCMS [M+H]$^+$ m/z: calc'd 438.2; found 438.3.

Step 5: Synthesis of Methyl 7-Chloro-2-(Trans-4-(Dimethylamino)Cyclohexyl)-2,4-Dimethyl-6-(2-Oxoethyl) Benzo[d][1,3]Dioxole-5-Carboxylate To a solution of methyl 7-chloro-2-(trans-4-(dimethylamino)cyclohexyl)-64(E)-2-ethoxyvinyl)-2,4-dimethylbenzo[d][1,3]dioxole-5-carboxylate (4.4 g, 10.0 mmol) in acetonitrile (63 mL) was added cerium chloride heptahydrate (18.6 g, 50.0 mmol), sodium iodide (7.49 g, 50.0 mmol) and water (100 μL). The reaction mixture was stirred at 80° C. for 3 h, then filtered through a plug of celite. The resulting filtrate was used directly in the next step. LCMS [M+H]$^+$ m/z: calc'd 410.17; found 410.3.

Step 6: Synthesis of Methyl 7-Chloro-2-(Trans-4-(Dimethylamino)Cyclohexyl)-2,4-Dimethyl-6-(2-Oxoethyl) Benzo[d][1,3]Dioxole-5-Carboxylate To the crude solution of methyl 7-chloro-2-(trans-4-(dimethylamino)cyclohexyl)-2,4-dimethyl-6-(2-oxoethyl) benzo[d][1,3]dioxole-5-carboxylate in acetonitrile (from the previous step) was added 3-(aminomethyl)-6-methyl-4-(methylsulfanyl)-1,2-dihydropyridin-2-one (free base) (3.68 g, 20.0 mmol) and triethylamine (3 mL, 21.5 mmol). The reaction mixture was stirred for 5 min at room temperature before sodium cyanoborohydride (3.14 g, mmol) was added. The reaction was stirred at room temperature for 5 min (or until complete consumption of the starting material) then quenched with a saturated solution of sodium bicarbonate. Next, the desired product was extracted with dichloromethane three times. The combined organic layers were then washed with brine, dried over sodium sulfate, filtered and concentrated to dryness under reduced pressure to give the title compound as a solid which was used in the next step without further purification. LCMS [M+H]$^+$ m/z: calc'd 578.24; found 578.4.

Step 7: Synthesis of 9-Chloro-2-(Trans-4-(Dimethylamino)Cyclohexyl)-2,4-Dimethyl-6-((6-Methyl-4-(Methylthio)-2-Oxo-1,2-Dihydropyridin-3-Yl)Methyl)-7,8-Dihydro-[1,3]Dioxolo[4,5-g]Isoquinolin-5(6H)-One To a crude solution of methyl 7-chloro-2-(trans-4-(dimethylamino)cyclohexyl)-2,4-dimethyl-6-(2-oxoethyl)benzo[d][1,3]dioxole-5-carboxylate in dimethyl sulfoxide (50 mL) was added potassium carbonate (1.38 g, 10.0 mmol). The reaction mixture was stirred at room temperature for 30 min (or until the starting material was completely consumed) then quenched with a saturated solution of sodium bicarbonate. Next, the desired product was extracted with dichloromethane three times. The combined organic layers were then washed with brine, dried over sodium sulfate, filtered and concentrated to dryness under reduced pressure. The residue was purified by reverse phase C18 column (gradient 30 to 70% acetonitrile in water with 0.1% trifluoroacetic acid) to give the title compound as a racemic mixture) (1600 mg, 29% yield over three steps) as a white solid.

The racemic mixture of (R)-9-chloro-2-(trans-4-(dimethylamino)cyclohexyl)-2,4-dimethyl-6-((6-methyl-4-(methylthio)-2-oxo-1,2-dihydropyridin-3-yl)methyl)-7,8-dihydro-[1,3]dioxolo[4,5-g]isoquinolin-5(6H)-one and (S)-9-chloro-2-(trans-4-(dimethylamino)cyclohexyl)-2,4-dimethyl-6-((6-methyl-4-(methylthio)-2-oxo-1,2-dihydropyridin-3-yl) methyl)-7,8-dihydro-[1,3]dioxolo[4,5-g]isoquinolin-5(6H)-one (1.6 g of mixture) was resolved by preparative SFC [Column: Chiralpak IC (250x21 mm I.D., 10 m). Mobile phase A: CO$_2$/Mobile phase B: 1:1 methanol/dichloromethane mixture with 0.25% isopropylamine. Isocratic (70% mobile phase A and 30% mobile phase B). Flow rate: 70 g/min. Column temperature: 25° C.]. Example 1 Peak 1 (eutomer): Retention time=4.69 min. Recovery=264 mg, 33% yield, 99.7% ee, >99% purity (tan solid). LCMS [M+H]$^+$ m/z: calc'd 546.2; found 546.3. $^1$H NMR (400 MHz, chloroform-d) δ 12.34 (br. s., 1H), 6.00 (s, 1H), 4.88 (s, 2H), 3.38-3.28 (m, 2H), 2.83 (d, J=5.9 Hz, 2H), 2.54 (s, 3H), 2.46-2.25 (m, 12H), 2.03 (br. s., 4H), 1.83 (br. s., 1H), 1.62 (s, 3H), 1.27 (d, J=8.3 Hz, 5H). Example 1 Peak 2 (distomer): Retention time=5.33 min. 73% ee, 97.5% purity (tan solid). LCMS [M+H]$^+$ m/z: calc'd 546.2; found 546.3. $^1$H NMR (400 MHz, chloroform-d) δ 12.86-12.59 (m, 1H), 6.00 (s, 1H), 4.87 (s, 2H), 3.36-3.28 (m, 2H), 2.81 (t, J=6.4 Hz, 2H), 2.53 (s, 3H), 2.45 (s, 9H), 2.33 (s, 3H), 2.10 (br. s., 2H), 2.04 (dd, J=2.9, 8.8 Hz, 2H), 1.90-1.81 (m, 1H), 1.62 (s, 3H), 1.41-1.22 (m, 5H).

Example 2: 9-Chloro-2-(Trans-4-(Dimethylamino) Cyclohexyl)-2,4-Dimethyl-6-((6-Methyl-4-(Methylthio)-2-Oxo-1,2-Dihydropyridin-3-Yl)Methyl)-[1,3] Dioxolo[4,5-g]Isoquinolin-

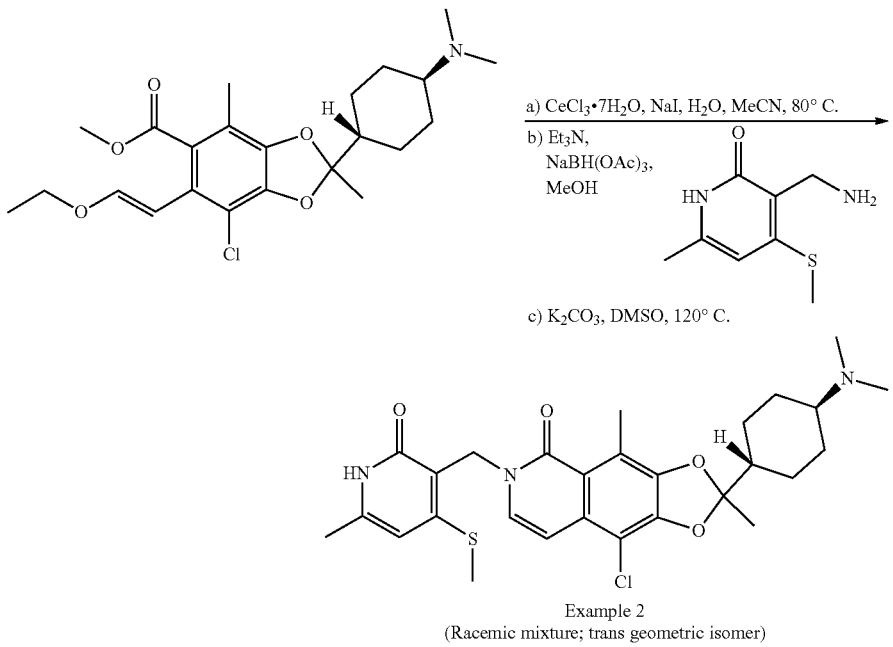

Example 2
(Racemic mixture; trans geometric isomer)

Step 8: Separation of (R)-9-chloro-2-(trans-4-(dimethylamino)cyclohexyl)-2,4-dimethyl-6-((6-methyl-4-(methylthio)-2-oxo-1,2-dihydropyridin-3-yl)methyl)-7,8-dihydro-[1,3]dioxolo[4,5-g]isoquinolin-5(6H)-one and (S)-9-chloro-2-(trans-4-(dimethylamino)cyclohexyl)-2,4-dimethyl-6-((6-methyl-4-(methylthio)-2-oxo-1,2-dihydropyridin-3-yl) methyl)-7,8-dihydro-[1,3]dioxolo[4,5-g]isoquinolin-5(6H)-one To a solution of methyl 7-chloro-2-(trans-4-(dimethylamino)cyclohexyl)-6-(2-ethoxyvinyl)-2,4-dimethylbenzo[d][1,3]dioxole-5-carboxylate (5.1 g, 11.6 mmol) (prepared according to the procedure described in Example 1 step 4) in acetonitrile (110 mL) was added cerium chloride heptahydrate (21.5 g, 57.9 mmol), sodium iodide (8.67 g, 57.9 mmol) and water (110 µL). The reaction mixture was stirred at 80° C. for 3 h, then filtered through a plug of celite. The resulting filtrate was concentrated under vacuum and used directly in the next step. The crude mixture was dissolved in 100 mL of methanol followed by addition of 3-(aminomethyl)-6-methyl-4-(methylsulfanyl)-1,2-dihydropyridin-2-one hydrochloride salt (5.96 g, 23.2 mmol) and triethylamine (6.43 mL, 46.4 mmol). This mixture was stirred at room temperature for 2 h (title compound could be observed by LCMS at this stage), then sodium cyanoborohydride (3.63 g, 57.9 mmol) was added to the reaction. The mixture was stirred for 1 h and then filtered through celite. The solid was rinsed with methanol (100 mL) and the filtrate was concentrated under reduced pressure to remove the methanol. Ethyl acetate (100 mL) and a saturated solution of sodium bicarbonate were added to the residue, and the desired product was extracted three times with ethyl acetate. The combined organic layers were then washed with brine, dried over sodium sulfate, filtered and concentrated to dryness under reduced pressure to give a mixture containing the title compound. This crude mixture was dissolved in dimethyl sulfoxide (50 mL) and potassium carbonate (3.2 g, 23.2 mmol) was added. The reaction mixture was stirred at room temperature for 30 min then a saturated solution of sodium bicarbonate was added. The desired product was extracted with dichloromethane three times and the combined organic layers were then washed with brine, dried over sodium sulfate, filtered and concentrated to dryness under reduced pressure. The residue was purified by a reverse phase C18 column (gradient 30 to 70% acetonitrile in water with 0.1% trifluoroacetic acid) to give the title compound (Example 2— racemic mixture) (356 mg, 5% yield) as a tan solid. LCMS [M+H]$^+$ m/z: calc'd 544.2; found 544.3. $^1$H NMR (400 MHz, chloroform-d) δ 13.26-13.11 (m, 1H), 7.11 (d, J=7.8 Hz, 1H), 6.62 (s, 1H), 6.00 (s, 1H), 5.18 (s, 2H), 2.76 (s, 3H), 2.42 (s, 3H), 2.34-2.28 (m, 9H), 2.24 (br. s., 1H), 2.01 (br. s., 3H), 1.89-1.82 (m, 1H), 1.66 (s, 3H), 1.33-1.21 (m, 5H).

The racemic mixture was separated into (R)-9-chloro-2-((1r,4R)-4-(dimethylamino)cyclohexyl)-2,4-dimethyl-6-((6-methyl-4-(methylthio)-2-oxo-1,2-dihydropyridin-3-yl)methyl)-[1,3]dioxolo[4,5-g]isoquinolin-5(6H)-one and (S)-9-chloro-2-((1r,4S)-4-(dimethylamino)cyclohexyl)-2,4-dimethyl-64(6-methyl-4-(methylthio)-2-oxo-1,2-dihydropyridin-3-yl)methyl)41,31dioxolo[4,5-g]isoquinolin-5(6H)-one by SFC [Chiralpak AD-H column (250×30 mm I.D., 5 μm). Mobile phase A: CO2/Mobile phase B: 2:5 ethanol/water with 0.1% ammonium hydroxide. Isocratic (85% mobile phase A and 15% mobile phase B). Flow rate: 50 mL/min. Column temperature: 40° C.]. Retention time: Peak 1 (distomer): 4.8 min. Peak 2 (eutomer): 6.5 min. Peak 1: 53.8 mg, 96.90 umol, 52.72% yield, 98% purity, >99% ee as a white solid. LCMS (M+H+) calcd.544.1; found 544.1H NMR (400 MHz, CD3OD) δ 6.91 (d, J=7.8 Hz, 1H), 6.61 (d, J=7.5 Hz, 1H), 6.20 (s, 1H), 5.18-4.86 (m, 2H), 2.61-2.55 (m, 3H), 2.40-2.31 (m, 3H), 2.23 (s, 3H), 2.21 (s, 7H), 1.92 (br d, J=6.5 Hz, 4H), 1.87-1.76 (m, 1H), 1.58 (s, 3H), 1.21 (br s, 4H) Peak 2: 37.6 mg, 68.41 umol, 37.22% yield, 99% purity, 97.6% ee as a white solid. LCMS (M+H+) calcd.544.2; found 544.1H NMR (400 MHz, CD3OD) δ 6.91 (d, J=7.5 Hz, 1H), 6.61 (d, J=7.5 Hz, 1H), 6.19 (s, 1H), 4.98 (s, 2H), 2.59 (s, 3H), 2.38 (s, 3H), 2.22 (s, 10H), 1.93 (br d, J=6.5 Hz, 4H), 1.82 (br s, 1H), 1.58 (s, 3H), 1.25-1.16 (m, 4H).

EZH2 Assays

IC$_{50}$ Measurements for Inhibitors Using EZH2

EZH2 biochemical assay (IC$_{50}$): Compound potencies were assessed through incorporation of $^3$H-SAM into a biotinylated H3 peptide. Specifically, 30 pM PRC2 containing wt EZH2 (pentameric complex prepared in-house) was pre-incubated with 450 nM SAM, 450 nM $^3$H-SAM, 2 μM H3K27me3 activating peptide (H$_2$N-RKQLATKAAR (Kme3)SAPATGGVKKP-amide) and compounds (as 10 point duplicate dose response titrations in DMSO, final assay 0.8% DMSO (v/v)) for 3-5 h in 50 mM Tris (pH 8.5), 1 mM DTT, 0.07 mM Brij-35, 0.1% BSA, and 0.8% DMSO in a total volume of 12.5 μl. Reaction was initiated with biotinylated H3 substrate peptide (H$_2$N-RKQLATKAAR (Kme1)SAPATGGVKKP-NTPEGBiot) as a 2 μM stock in 12.5 μl of buffer and allowed to react at room temperature for 18-22 h. Quenching was accomplished by addition of 20 μl of STOP solution (50 mM Tris (pH 8.5), 200 mM EDTA, 2 mM SAH). 35 μl of the quenched solution was transferred to streptavidin coated FlashPlates (PerkinElmer), incubated 1-2 h, washed, and read in a TopCount Reader (PerkinElmer). IC$_{50}$ s were calculated in Genedata Screener using non-linear least square four parameter fits, where the four parameters were IC$_{50}$, Hill slope, pre-transitional baseline (0% INH), and post-transitional baseline (100% INH).

EC$_{50}$ Measurements for Inhibitors in HeLa Cell Assays

H3K27me3 Alpha Hela Assay (AlphaLISA). Ten different doses of each test compound (in a series of 3-fold dilutions) were plated in duplicate 384-well tissue culture treated plates (Catalog #6007680; Perkin Elmer, Waltham, MA). Hela cells grown in culture were trypsinized and counted using a Countess® cell counter (Catalog #C10281; Life Technologies, Grand Island, NY). Cell were diluted to 67,000 cells per mL in10% DMEM (Catalog #10569-010 Life Technologies, Grand Island, NY) and 15 μL (1,000 cells) were plated into each well using the Biotek MicroFlo™ Select Dispenser (BioTek Instruments, Inc. Vermont, USA),) of the 384-well plate. Plates were incubated at 37° C./5% CO$_2$ for 72 hrs. One of the duplicate plates was processed for HeLa assay and the other for viability. 5 μL of Cell-Histone Lysis buffer (1X) (Catalog #AL009F1 Perkin Elmer; Waltham, MA) per well was added to the plate processed for AlphaLISA and the plate was incubated at RT for 30 minutes on a plate shaker with low speed (Model #4625-Q Thermo Scientific; Waltham, MA). Then, 10 μL per well Histone Extraction buffer (catalog #AL009F2; Perkin Elmer; Waltham, MA) was added and the plate further incubated at RT for 20 min on plate shaker with low speed. Next, 10 μL of 5X mix of anti-K27me3 acceptor beads plus Biotinylated anti-Histone H3 (C-ter) Antibody (diluted to 3 nM final) (Catalog #AL118 Perkin Elmer; Waltham, MA) was added in each well. Dilution of the acceptor beads and anti-Histone H3 was done in 1X Histone Detection buffer (Catalog #AL009F3 Perkin Elmer; Waltham, MA) which was produced by diluting the 10X stock provided. The plate was sealed with an aluminum plate sealer and incubated at 23° C. for 60 min. Next, 10 μL 5X solution of Streptavidin Donor beads were added (Catalog #6760002 Perkin Elmer; Waltham, MA) (20 μg/mL final in 1X Histone Detection Buffer), =plate was sealed with Aluminum plate sealer and incubated at 23° C. for 30 min. The plates were then read using an EnVision-Alpha Reader (model #2104 Perkin Elmer; Waltham, MA).

Cell viability was assayed by adding 15 μL of Cell Titer Glo ((Catalog #G9241 Promega Madison, WI) to each well with cells with media. The plates were incubated at RT for 15-20 minutes on a plate shaker at low speed. The plates were then read using an EnVision-Alpha Reader (model #2104 Perkin Elmer; Waltham, MA).

GI$_{50}$ Measurements for Inhibitors in Karpas-422 Viability Assays

Karpas-422 cell lines were obtained from DSMZ (Braunschweig, Germany) and were grown in RPMI-1640 media. All media contained 10% fetal bovine serum (FBS) and 1% penicillin/streptomycin (Invitrogen). 20K cells per well were plated onto 96 well compound coated plates. Cells were split and seeded at original plating density (based on the DMSO well counts) every 4 days into plates containing fresh EZH2 inhibitors. Relative cell numbers were assessed by Cell Titer-Glo luminescent cell viability assay (Promega) on Day 8. GraphPad Prism 5 was used for curve fitting and GI$_{50}$ values were reported. Data is shown in Table 1.

TABLE 1

| Example | EZH2 IC$_{50}$ (pM) | HeLa EC$_{50}$ (nM) | Karpas-422 GI$_{50}$ (nM) |
|---|---|---|---|
| Example 1, Peak 1 (single enantiomer, trans geometric isomer) | 26 to 87 | 0.849 to 1.13 | 5.7 |
| Example 1, Peak 2 (single enantiomer, trans geometric isomer) | 178 to 278 | — | — |
| Example 2 (racemic mixture, trans geometric isomer) | 61 to 73 | — | — |
| Example 2, Peak 1 (single enantiomer, trans geometric isomer) | 4470 | | |
| Example 2, Peak 2 (single trans geometric isomer) | 25 | | |

The invention claimed is:

1. A compound of the Formula:

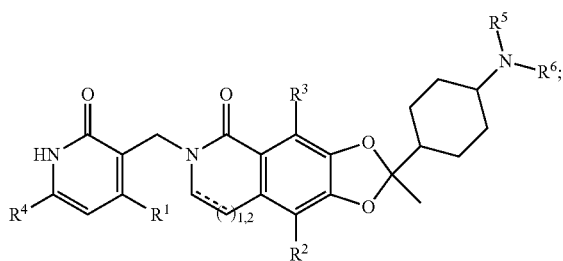

or a pharmaceutically acceptable salt thereof, wherein
R$^1$ is halo, (C$_1$-C$_4$)alkyl, halo(C$_1$-C$_4$)alkyl, —O(C$_1$-C$_4$)alkyl, or —O[halo(C$_1$-C$_4$)alkyl], —S(C$_1$-C$_4$)alkyl, or —S[halo(C$_1$-C$_4$)alkyl];
R$^2$ is hydrogen, halo, or (C$_1$-C$_4$)alkyl;
R$^3$ is (C$_1$-C$_4$)alkyl or halo(C$_1$-C$_4$)alkyl;
R$^4$ is halo, (C$_1$-C$_4$)alkyl, or halo(C$_1$-C$_4$)alkyl;
R$^5$ is hydrogen, (C$_1$-C$_4$)alkyl, or halo(C$_1$-C$_4$)alkyl;
R$^6$ is halo, (C$_1$-C$_4$)alkyl, or halo(C$_1$-C$_4$)alkyl; or
R$^5$ and R$^6$ together with the nitrogen atom to which they are attached form a 4- to 7-membered heterocyclyl optionally substituted with 1 to 3 groups selected from halo, (C$_1$-C$_4$)alkyl, halo(C$_1$-C$_4$)alkyl, and —OW;
R$^7$ is (C$_1$-C$_4$)alkyl, halo(C$_1$-C$_4$)alkyl, or (C$_3$-C$_7$)cycloalkyl; and
the dashed line represents a single or double bond.

2. The compound of claim 1, wherein the compound is of the Formula:

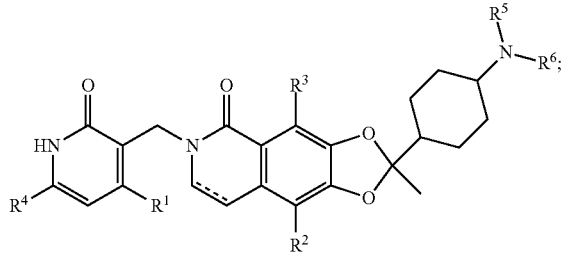

or a pharmaceutically acceptable salt thereof.

3. The compound of claim 1, wherein the compound is of the Formula:

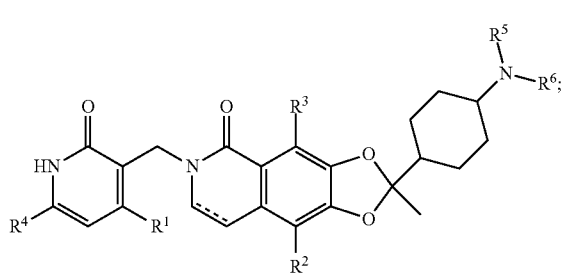

or a pharmaceutically acceptable salt thereof.

4. The compound of claim 1, wherein the compound is of the Formula:

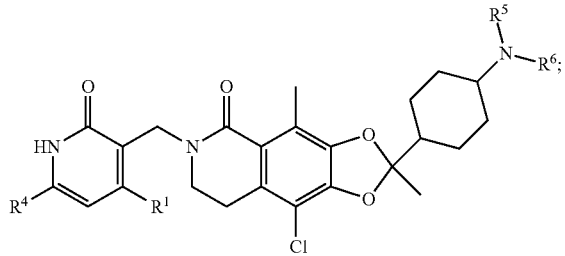

or a pharmaceutically acceptable salt thereof.

5. The compound of claim 1, wherein R$^1$ is halo or —S(C$_1$-C$_4$)alkyl.

6. The compound of claim 1, wherein R$^4$ is halo or (C$_1$-C$_4$)alkyl.

7. The compound of claim 1, wherein R$^5$ is (C$_1$-C$_4$)alkyl.

8. The compound of claim 1, wherein R$^6$ is (C$_1$-C$_4$)alkyl.

9. The compound of claim 1, wherein R$^5$ and R$^6$ are each methyl.

10. The compound of claim 1, wherein the group

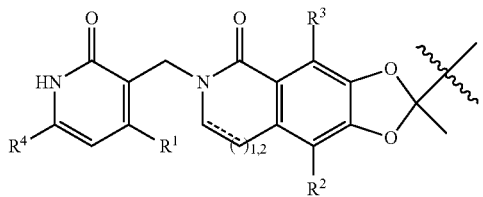

and NR⁵R⁶ are oriented trans about the cyclohexyl.

11. The compound of claim 1, wherein the group

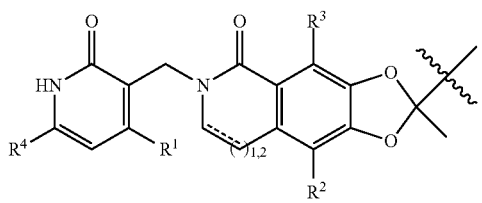

and NR⁵R⁶ are oriented cis about the cyclohexyl.

12. The compound of claim 1, wherein the stereochemical configuration of the chiral center of the 1,3-dioxolanyl is R.

13. The compound of claim 1, wherein the stereochemical configuration of the chiral center of the 1,3-dioxolanyl is S.

14. The compound of claim 1, wherein the compound is of the Formula:

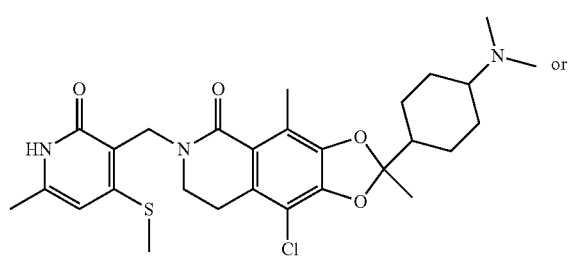

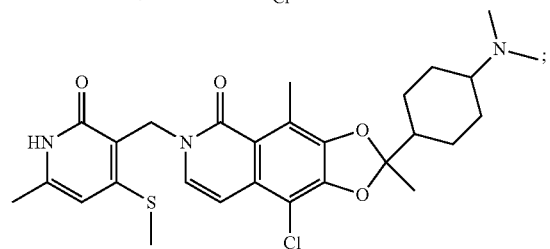

or a pharmaceutically acceptable salt thereof.

15. The compound of claim 1, wherein the compound is of the Formula:

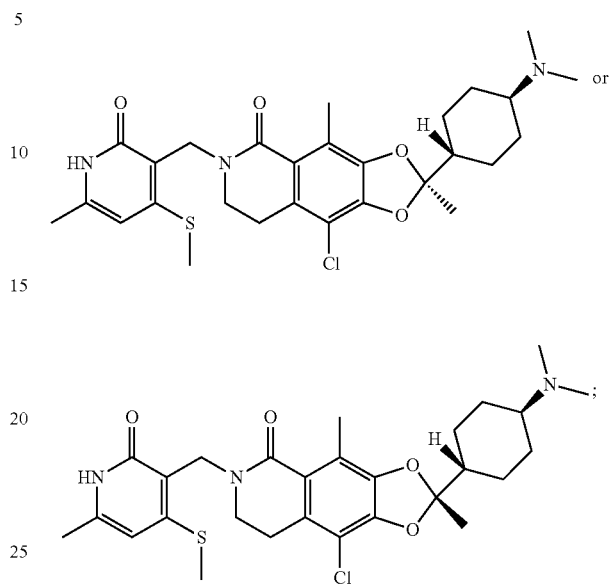

or a pharmaceutically acceptable salt thereof.

16. A pharmaceutical composition comprising the compound of claim 1, or a pharmaceutically acceptable salt thereof; and a pharmaceutically acceptable carrier.

17. A method for treating cancer in a subject, comprising administering to the subject an effective amount of a compound of claim 1, or a pharmaceutically acceptable salt thereof.

18. The method of claim 17, wherein the cancer is selected from breast cancer, prostate cancer, colon cancer, renal cell carcinoma, glioblastoma multiforme cancer, bladder cancer, melanoma, bronchial cancer, lymphoma, leukemia, cholangiocarcinoma, sarcoma, multiple myeloma, lung cancer, ovarian cancer, stomach cancer, adenoid cystic carcinoma and liver cancer.

* * * * *

UNITED STATES PATENT AND TRADEMARK OFFICE
CERTIFICATE OF CORRECTION

PATENT NO. : 11,919,912 B2
APPLICATION NO. : 17/057225
DATED : March 5, 2024
INVENTOR(S) : Alexandre Côté et al.

It is certified that error appears in the above-identified patent and that said Letters Patent is hereby corrected as shown below:

In the Claims

At Column 21, Claim number 1, Line number 64, recites:
"-OW;"
It should recite:
"-OR$^7$;"

At Column 22, Claim number 3, Line number 25-36, recites:

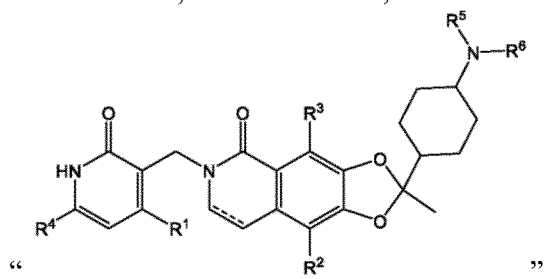

It should recite:

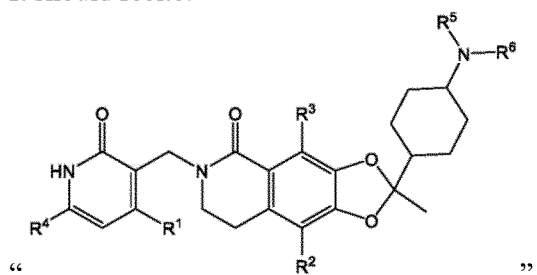

Signed and Sealed this
Twenty-seventh Day of August, 2024

Katherine Kelly Vidal
*Director of the United States Patent and Trademark Office*